United States Patent [19]

Mallavarapu

[11] Patent Number: 4,996,284

[45] Date of Patent: Feb. 26, 1991

[54] NOVEL EPOXY SULFONAMIDE-BASED RESINS, A PROCESS FOR THEIR PREPARATION AND USE OF SAME

[76] Inventor: Leo X. Mallavarapu, 32 Tamarack La., Pomona, N.Y. 10970

[21] Appl. No.: 342,170

[22] Filed: Apr. 24, 1989

[51] Int. Cl.$^5$ .............................................. C08G 59/44
[52] U.S. Cl. ........................................ 528/92; 528/93; 528/109; 528/361; 528/391
[58] Field of Search ............ 528/92, 93, 109, 361'391; 564/82

[56] References Cited

U.S. PATENT DOCUMENTS

| | | | |
|---|---|---|---|
| 2,712,001 | 6/1955 | Greenlee | 528/109 X |
| 3,277,050 | 10/1966 | Pettigrew | 528/109 |
| 3,819,581 | 6/1974 | Smith | 528/109 |
| 3,849,375 | 11/1974 | Smith | 528/109 |
| 4,528,359 | 7/1985 | Berman et al. | 528/109 |
| 4,618,526 | 10/1986 | Berman et al. | 528/109 X |

*Primary Examiner*—Earl Nielsen
*Attorney, Agent, or Firm*—Edwin D. Schindler

[57] ABSTRACT

A process for the preparation of a sulfonamide-based epoxy resinous composition, which includes the step of reacting a sulfonamide compound with a resinous composition containing a plurality of epoxide groups in the presence of a Lewis acid, is disclosed. The epoxy sulfonamide resins of the invention, which are being claimed, have applications in nail lacquer compositions and other cosmetics, adhesives, and in wood and paper coatings, as a plasticizer and as a modifier in injection molding applications for various resins.

6 Claims, No Drawings

NOVEL EPOXY SULFONAMIDE-BASED RESINS, A PROCESS FOR THEIR PREPARATION AND USE OF SAME

BACKGROUND OF THE INVENTION

1. Technical Field of the Invention

The present invention relates to the new epoxy sulfonamide-based resins. More particularly, the present invention provides a series of novel epoxy sulfonamide resins and a process for their synthesis. The present invention substitutes for aldehydes, e.g., formaldehyde, as presently used in the synthesis of aryl sulfonamide resins, a plurality of non-toxic and environmentally safe epoxy polymers. The epoxy sulfonamide resins of the invention have applications in nail lacquer compositions and other cosmetics, adhesives, and in wood and paper coatings, as a plasticizer and as a modifier in injection molding applications for various resins. Additional applications will be discussed hereinafter.

2. Description of the Prior Art

It is presently known to the art that numerous types of resins may be formed by the condensing of various sulfonamides with aldehydes, such as formaldehyde, furfuraldehyde and acetaldehyde. Aryl sulfonamides condensates have been considered in the literature as super-cooled organic glasses. McMaster, L., *J. Am. Chem. Soc.* 56, 204 (1934); Walter, G., *Trans. Faraday Soc.*, 32, 406 (1936).

The earliest application of sulfonamides as nitrocellulose plasticizers was disclosed by Schmidt, U.S. Pat. No. 758,335, issued Apr. 26, 1904, wherein such sulfonamides replaced the use of camphor. See, Hyatt, U.S. Pat. No. 105,338.

The use of sulfonamide aldehyde resins in film forming compositions with cellulose esters and esters was, apparently, first taught by H. A. Gardner, U.S. Pat. No. 1,564,664, issued Apr. 7, 1925.

It is, further, generally known in the art that aryl sulfonamides and aryl sulfonamide aldehyde resins are compatible, to varying degrees, with a variety of other types of resins. Depending upon the degree of plasticization, the physical properties of the resins may be so enhanced. Properties of the plasticized resins which may be improved include, flexibility, resistance to water permeability, strength, brilliance, elongation, toughness, adhesion and gloss. Examples of resins whose properties are improved by plasticizing sulfonamides and sulfonamide aldehyde resins includes, e.g., cellulose nitrate, cellulose acetate, ethyl cellulose, nylon, zein, and cellulose acetate butyrate.

The improvement in physical properties is believed to be evident with respect to the properties of films, as well as in injection molded articles. In particular, the toluene sulfonamide formaldehyde-based resins have found a niche in the coatings industry for use as a component in wood finishes, paper coatings, and barrier cating for cellophane. Such resins have also found wide use in coatings which may come into contact with food. One particularly useful and important application of such resins, which has proliferated in recent years, is their use as a component in nail lacquer composition for cosmetics. In this application, superior properties of the sulfonamide resins are evident in the enhanced brilliance, gloss clarity, adhesion, flexibility and resistance-to-water-spotting conferred on the plasticized nitrocellulose film that results.

During the past several years, there has been a growing concern about the use of any type of aldehyde condensate, particularly, formaldehyde condensates, both in the workplace and in the area of consumer products, be it adhesives, coatings, e.g., textile coatings, or in the formulation and application of cosmetics, etc. This growing concern, in part, is attributable to research which has determined that formaldehyde is suspected to be a human carcinogen.

In an effort to replace the use of sulfonamide formaldehyde resins with less toxic substitutes, rosin esters, acrylic resins, polyester resins and certain emulsion type resins have been used. The use of such substitutes, however, has been less than satisfactory in result. Invariably, the finished formulation would have numerous drawbacks in performance characteristics including, but not limited to, adhesion, gloss, water resistance, brilliance and clarity of film.

The "brilliance" exhibited by toluene sulfonamide apparently carries through to resinous products formed by the reaction of toluene sulfonamide with appropriate reactants which, in the foregoing instances, clearly do not contain any sulfonamides.

It is speculated by the inventor that the clarity and brilliance exhibited by those formulations utilizing sulfonamide-based resins are attributable to the refractive index of the sulfonamides themselves.

The solubility and long-term stability of sulfonamide formaldehyde resins, especially in n-butyl acetate, has always been a very important characteristic for use in nail lacquer formulations. These formulations contain cellulose nitrate and the sulfonamide resins act as plasticizers, conferring desirable properties in the end product.

There is presently a need, thus far unfulfilled, for sulfonamide resins, which exhibit the foregoing beneficial properties, yet do not contain formaldehyde and the inherent drawbacks attendant with its use. Heretofore, the use of formaldehyde has been required as a reactant in the synthesis of sulfonamide resins.

SUMMARY OF THE INVENTION

It is, therefore, an object of the present invention to provide an aryl or aliphatic sulfonamide-based resin, for use in cosmetics, among a wide variety of other applications, which neither contains formaldehyde nor requires reaction with formaldehyde in its synthesis.

It is, yet, an additional object of the present invention to provide an aryl or alphatic sulfonamide-based resin that would be highly stable in its numerous applications.

It is still a further object of the present invention to provide an aryl or aliphatic sulfonamide-based resin which is non-toxic and environmentally safe.

It is an additional object of the present invention to provide a process for the synthesis of a non-formaldehyde, aryl or aliphatic sulfonamide-based resin which is economical to carry out.

It is a further object of the present invention to overcome the drawbacks inherent in the prior art.

The foregoing and related objects are achieved by a process for the preparation of sulfonamide-based oligomer and polymer resins which substitutes for formaldehyde a class of environmentally safe, i.e., non-toxic, epoxy polymers which are made to react with aryl or aliphatic sulfonamides in the presence of a Lewis acid, such as tetramethyl ammonium chloride, tetramethyl ammonium bromide, zinc chloride, aluminum chloride, etc. Examples of appropriate epoxy resins which may be used in combination with the present invention include diglycidyl ether bisphenol A type, with a molecular weight of up to approximately 20,000; epoxy resins of the diglycidyl bisphenol F type, with a molecular weight of up to approximately 20,000; and, epoxy resins of a type where the backbone is formed by vinyl copolymerication and the epoxy group is present and available for further reaction. Examples of aryl sulfonamides which may be employed in the synthesis reaction of the present invention include benzene-sulfonamide, toluenesulfonamide, naphthalene sulfonamide, chlorobenzene sulfonamide, nitrobenzenesulfonamide, phenyl methane sulfonamide, benzene disulfonamide and naphthalene disulfonamide. In addition, aliphatic sulfonamides may be utilized for the production of non-aryl sulfonamide resins, such as, for example, methane sulfonamide and ethane sulfonamide.

The synthesis process of the invention is carried out in the presence of a Lewis acid without which, it was surprisingly discovered, the reaction between the sulfonamide and the epoxy polymer could not take place. Conventional processes, in contrast to the present invention, which are carried out substantially without the presence of a Lewis acid, must necessarily rely upon an aldehyde as a reactant, in most cases, formaldehyde, in order that the required reaction may be initiated.

Aside from the substitution of formaldehyde in its various forms, e.g., 37% $CH_2O$, 44% $CH_2O$, 50% $CH_2O$, paraformaldehyde, in the present invention with an appropriate epoxy polymer and a Lewis acid catalyst, the process proceeds under reaction condition similar to those existing in prior art procedures, except that it goes up to temperatures, e.g., 220° C., where the sulfonamide-formaldehyde resins decompose releasing formaldehyde.

The resins produced by the synthesis process according to the present invention exhibit compatibility with nitrocellulose and other cellulosics thereby eliminating environmental concerns which are otherwise present when formaldehyde-based sulfonamide resins are employed.

A further advantage resulting from the present invention is that the reaction product of the mixed or pure sulfonamides with the class of epoxy reactants of the present invention are indefinitely stable in n-butyl acetate solutions, in which such reaction products are often later used.

The present invention will now be described in further detail with reference being made to the following experimental examples. It should, however, be realized that the following examples are intended as being only illustrative of the procedures of the present invention and are not intended as a means for defining the scope thereof.

In the following examples, where pure P-toluene sulfonamide is cited as a reactant, mixtures containing para- and ortho-toluene sulfonamide, in any ratio, may be substituted with substantially similar results.

EXAMPLE 1

A 2 liter three-neck flask, fitted with an agitator and a thermometer along with provision for blanketing with nitrogen gas was set up with a heating mantle. To this was added 342 grams of pure p-toluene sulfonamide followed by 875 grams of a solid epoxy resin (a polymeric diglycidyl ether of bisphenol A) E.E.W. 437.5.

The product was melted to a clear solution in approximately a half hour with stirring and a nitrogen blanket and slowly allowed to be heated to approximately 180° C. (356° F.). It was kept at this temperature for 10 minutes and the material was poured out into an aluminum pan and allowed to cool. A sticky mass was obtained with apparently no reaction having taken place.

EXAMPLE 2

Example 1 was repeated with same quantities of materials except when the temperature was 140° C., 400 mg of a 50% solution of tetramethyl ammonium chloride in water was added.

Slow heating was continued from this temperature with stirring and the heating mantle removed when an exotherm started to take place. Some foaming was observed due to the water boiling over in the viscous mass and when the temperature reached about 360° F. the foaming subsided (half hour). The material was then poured into an aluminum pan and allowed to cool.

The resin was brittle and clear and could be broken into non-blocking particles. The softening point by the capillary method was 82° C.

In the absence of tetramethyl ammonium chloride no resin formation takes place.

An 80% solution of this resin was made by heating in butyl acetate. A clear viscous solution was obtained. The viscosity of the solution was in excess of Z2 (Gardner-Holdt at 25° C). The solution was compatible with the standard nitrocellulose solutions.

EXAMPLE 3

Example 2 was repeated with the same quantities of material except in the place of tetramethyl ammonium chloride 500 mg of zinc chloride in 50% solution was used with similar results.

EXAMPLE 4

Example 2 was repeated except in the place of tetramethyl ammonium chloride 500 mg of tetramethyl ammonium bromide in a 50% solution was used with similar results.

EXAMPLE 5

Example 2 was repeated except in the place of tetramethyl ammonium chloride 350 mg of ammonium chloride hexahydrate crystals was used with similar results.

EXAMPLE 6

Example 2 was repeated except the epoxy resin had an E.E.W. of 189. Upon addition of the tetramethyl ammonium chloride at 140° C. within a few minutes a very vigorous exotherm started to take place with the temperature climbing to 220° C. within a period of 3 to 5 minutes. The heating mantle was quickly removed and the flask was cooled with warm water to keep the temperature from going beyond 220° C. It was noted that the resin formation takes place at approximately 198° C. The cooled sample becomes brittle. (When the experiment was repeated without tetramethyl ammonium chloride it was noted that no resin formation takes place.)

The material was poured out onto an aluminium pan and allowed to cool forming a clear glass-like tack free mass which was easily broken into small pieces.

An 80% solution of this material in n-butyl acetate solution was exceptionally clear and had a viscosity in excess of Z2 (Gardner-Holdt.)

EXAMPLE 7

Example 6 was repeated except in place of tetramethyl ammonium chloride, 500 mg of tetramethyl ammonium bromide in a 50% solution was substituted and similar results were obtained.

EXAMPLE 8

Example 6 was repeated except in place of tetramethyl ammonium chloride, 500 mg of tetramethyl ammonium bromide in a 50% solution was substituted and similar results were obtained.

EXAMPLE 9

Example 6 was repeated except in place of tetramethyl ammonium chloride, 350 mg of aluminium chloride hexahydrate crystals was substituted and similar results were obtained.

The following formulations illustrate the compatibility of these new products produced in Examples 2 through 9 in several coating applications:

| Formulation A - Adhesive 1 | |
|---|---|
| Components | Parts by Weight |
| Polyvinyl acetate emulsion | 100 |
| Sulfonamide-epoxy resin (80% solution in n-BuAc) | 13.5 |
| Butyl benzyl phthalate | 9 |
| Water | 13.4 |

This adhesive formulation can be used for bonding aluminium to paper, as well as to itself.

| Formulation B - Adhesive 2 | |
|---|---|
| Components | Parts by Weight |
| Cellulose acetate-butyrate (½ sec) | 100 |
| Sulfonamide-epoxy resin | 100 |
| Ethanol | 100 |
| Isobutyl Acetate | 67 |
| Toluene | 233 |
| Hi-Flash Napatha | 67 |

This adhesive formulation may be used for sealing paper to other cellulosic materials.

| Formulation C - High Gloss Paper Lacquer | |
|---|---|
| Components | Parts by Weight |
| Cellulose Acetate Butyrate (½ sec) | 100 |
| Sulfonamide-epoxy resin | 50 |
| Ethanol | 50 |
| Isobutyl Acetate | 50 |
| Acetone | 50 |
| Toluene | 200 |

| Formulation D - Clear Nitrocellulose Wood Lacquers | |
|---|---|
| Components | Parts by Weight |
| R.S. ½ sec nitrocellulose | 100 |
| Sulfonamide-epoxy resin | 100-200 |
| Butyl benzyl phthalate | 50 |
| Ethanol | 200 |
| Butyl acetate | 800 |
| Toluene | 1000 |

| Formulation E - Nail Lacquer | | |
|---|---|---|
| Components | Base (%) | Top Coat (%) |
| RS ½ sec nitrocellulose | 10 | 15 |
| Sulfonamide-epoxy resin | 12 | 5 |
| (80% in solution in n-BuAc) | | |
| Butyl benzyl phthalate | 4 | 4 |
| Ethyl alcohol | 5 | 10 |
| Ethyl acetate | 20 | 10 |
| Buty acetate | 13 | 10 |
| Toluene | 36 | 45 |

On the basis of the foregoing illustrative formulations, it has been determined that the resinous reaction products of the present invention, which are made using an epoxy resin condensate of various sulfonamides, perform well in the formulations intended for applications, such as nail lacquers, adhesives and wood and paper coatings. It has further been discovered that the epoxy sulfonamide condensate exhibits as good, if not superior, properties in performance in the areas of adhesion, flexibility, clarity, gloss, water permeability, water spotting, film strength, elongation and toughness. The epoxy sulfonamide condensates of the invention have the advantage of being able to be substituted on an almost weight-for-weight basis in existing formulations utilizing sulfonamide formaldehyde resins, such as Santolite MHP or MS-80 (trademarks of Monsanto company, St. Louis, Mo.)

In addition, the formulations according to the present invention have the added advantage that upon decomposition by thermal means the formulations containing the resins of the invention do not decompose to produce noxious formaldehyde vapors.

While only several embodiments of the present invention have been shown and described, it should be obvious to those skilled in the art that many modifications may be made to the present invention without departing form the spirit and scope thereof.

What is claimed is:

1. A process for the preparation of a thermoplastic sulfonamide-based epoxy resinous composition, comprising the step of:
    reacting a sulfonamide compound with a resinous composition, at a temperature of, at least, approximately 140° C. containing a plurality of epoxide groups in the presence of a Lewis acid.

2. The process according to claim 1, wherein said sulfonamide compound is an aryl sulfonamide compound.

3. The process according to claim 1, wherein said sulfonamide compound is a member selected from the group consisting of benzene-sulfonamide, toluenesulfonamide, naphthalene sulfonamide, chlorobenzene sulfonamide, nitrobenzenesulfonamide, phenyl methane sulfonamide, benzene disulfonamide, naphthalene disulfonamide, methane sulfonamide and ethane sulfonamide.

4. The process according to claim 1, wherein said resinous composition containing a plurality of epoxide groups includes diglycidyl ether bis phenol A type with a molecular weight of up to approximately 20,000.

5. The process according to claim 1, wherein said resinous composition containing a plurality of epoxide groups includes diglycidyl bis phenol F type with a molecular weight of up to approximately 20,000.

6. The process according to claim 1, wherein said Lewis acid is a member selected from the group consisting of tetramethyl ammonium chloride, tetramethyl ammonium bromide, zinc chloride and aluminum chloride.

* * * * *